(12) United States Patent
King et al.

(10) Patent No.: US 7,605,137 B2
(45) Date of Patent: Oct. 20, 2009

(54) COMBINATION THERAPY COMPRISING CLORETAZINE

(75) Inventors: Ivan King, North Haven, CT (US); Mario Sznol, Woodbridge, CT (US); Michael Belcourt, Wallingford, CT (US); Li-Mou Zheng, Orange, CT (US)

(73) Assignee: Vion Pharmaceuticals, Inc., New Haven, CT (US)

( * ) Notice: Subject to any disclaimer, the term of this patent is extended or adjusted under 35 U.S.C. 154(b) by 145 days.

(21) Appl. No.: 10/593,217

(22) PCT Filed: Mar. 25, 2005

(86) PCT No.: PCT/US2005/010152

§ 371 (c)(1), (2), (4) Date: Sep. 15, 2006

(87) PCT Pub. No.: WO2005/094282

PCT Pub. Date: Oct. 13, 2005

(65) Prior Publication Data

US 2008/0025984 A1    Jan. 31, 2008

Related U.S. Application Data

(60) Provisional application No. 60/556,565, filed on Mar. 26, 2004.

(51) Int. Cl.
*A61K 31/175* (2006.01)
*A61K 31/52* (2006.01)
*A61K 31/505* (2006.01)

(52) U.S. Cl. ............... 514/43; 514/45; 514/46; 514/50; 514/86; 514/274; 564/35

(58) Field of Classification Search ........... 514/43, 514/45, 46, 50, 86, 274; 564/35
See application file for complete search history.

(56) References Cited

U.S. PATENT DOCUMENTS

| | | | |
|---|---|---|---|
| 4,175,200 A | 11/1979 | Hunter et al. | |
| 4,385,055 A | 5/1983 | Klayman et al. | |
| 4,447,427 A | 5/1984 | Klayman et al. | |
| 4,684,747 A | 8/1987 | Satorelli et al. | |
| 4,696,938 A | 9/1987 | Le | |
| 4,849,563 A | 7/1989 | Satorelli et al. | |
| 5,101,072 A | 3/1992 | Satorelli et al. | |
| 5,214,068 A | 5/1993 | Satorelli et al. | |
| 5,256,820 A | 10/1993 | Satorelli et al. | |
| 5,637,619 A | 6/1997 | Satorelli et al. | |
| 5,767,134 A | 6/1998 | Li et al. | |
| 5,919,816 A * | 7/1999 | Hausheer et al. | 514/449 |
| 6,040,338 A | 3/2000 | Satorelli et al. | |
| 6,630,480 B1 * | 10/2003 | Gourdeau et al. | 514/274 |
| 6,696,487 B2 | 2/2004 | Gerusz et al. | |
| 6,855,695 B2 | 2/2005 | Lin et al. | |
| 2005/0043244 A1 | 2/2005 | Lin et al. | |

FOREIGN PATENT DOCUMENTS

| | | |
|---|---|---|
| CN | 101014353 A | 8/2007 |
| EP | 1804816 A2 | 7/2007 |
| HK | 1107775 | 4/2008 |
| WO | WO/02/30424 | 4/2002 |
| WO | WO 2005/094282 | 10/2005 |

OTHER PUBLICATIONS

Lee et al, International Journal of Toxicology, 2002, 21, 23-38.*
Baumann RP, et al., 2004, "1,2-Bis(methylsulfonyl)-1-(2-chloroethyl)-2-[(methylamino)carbonyl]hydrazine (VNP40101M): II. Role of O6-alkylguanine-DNA alkytransferase in cytotoxicity." Cancer Chemother Pharmacol. 53(4):288-295.
Burchenal, et al., 1988, "Cancer: the Outlaw Cell," ed. Richard E Lafond, American Chemical Society: 204-205.
Gura, et al., 1997, "Systems for identifying new drugs are often faulty," Science: 278(5340):1041-2.
Lee, et al., 2002, "Toxicological evaluation of 1,2 bis(methylsulfonyl)-1-(2-chloroethyl)-2(methylaminocarbonyl) hydrazine (VNP40101M), novel alkylating Agent with Potential Antitumor Activity, with Intravenous Administration in Rats and Dogs", Interntional Journal of Toxicology. vol. 23: 23-39.
Hrubiec, et al., 1986, "Synthesis and evaluation of 1 -(arylsulfonyl)-2-[(methoxycarbonyl)sulfenyl]-1 methylhydrazines ++ + as antineoplastic agents." J Med Chem. 29(9):1777-9.

(Continued)

*Primary Examiner*—Shaojia Anna Jiang
*Assistant Examiner*—Ganapathy Krishnan
(74) *Attorney, Agent, or Firm*—Law Offices of Albert Wai-Kit Chan, PLLC

(57) ABSTRACT

This invention provides a method for treating tumor in a subject comprising administering to the subject an effective amount of: (1) VNP40101M, or its equivalent; and (2) a nucleoside, or a nucleoside analog. This invention also provides a method for inhibiting tumor cell growth comprising contacting the tumor cell with effective amounts of: (1) VNP40101M, or its equivalent; and (2) a nucleoside, or a nucleoside analog. The present invention relates to the treatment of cancer, comprising administering to a subject in need thereof an effective amount of VNP40101M in combination with a nucleoside.

15 Claims, No Drawings

OTHER PUBLICATIONS

Hrubiec, et al., 1986, "Synthesis and evaluation of 2-substituted 1-methyl-1-(4-tolysulfonyl)hydrazines as antineoplastic agents," J Med Chem. 29(7):1299-301.

Murren, et al., 2005, "A phase I and pharmacokinetic study of VNP40101M, a new alkylating agent, in patients with advanced or metastatic cancer", Investigational New Drugs. vol. 23: 123-135.

Mao, et al., 2002, "Pharmacokinetics, Mass Balance, and Tissue Distribution of a Novel DNA Alkylating Agent, VNP40101M, in Rats", AAPS PharmSci: 4(4)24.

Penketh, et al., 1994, "Studies on the mechanism of decomposition and structural factors affecting the aqueous stability of 1,2-bis-(sulfonyl)-1-alkylhydrazines", J Med Chem 37: 2912-2917.

Penketh, et al., 2000, "Comparison of DNA lesions produced by tumor-inhibitory 1,2-bis(sulfonyl)hydrazines and chloroethylnitrosoureas", Biochem Pharmacol 59:283-91.

Pratviel, et al., 1989, "Cytotoxic and DNA-damaging Effects of 1,2-bis(sulfonyl)hydrazines on Human Cells of the Mer+ and Mer− phenotype", Cancer Biochem Biophys 10:365-75 (abstract only).

Shyam, et al., 1985, "Synthesis and evaluation of N,N'-bis(arylsulfonyl)hydrazines as antineoplastic agents" J Med Chem 28:525-7.

Shyam, et al., 1986, "1,2-bis(arylsulfonyl)hydrazines. 2. The influence of arylsulfonyl and aralkylsulfonyl substituents on antitumor and alkylating activity", J Med Chem 29:1323-5.

Shyam, et al., 1987, "1,2-Bis(sulfonyl)hydrazines. 3. Effects of structural modification on antineoplastic activity", J Med Chem 30:2157-61.

Shyam, et al., 1990, "Synthesis and evaluation of 1,2,2-tris-(sulfonyl)hydrazines as antineoplastic and trypanocidal agents", J Med Chem 33(8):2259-64.

Shyam, et al., 1993, "Synthesis and evaluation of 1-acyl-1,2-bis(methylsulfonyl)-2-(2- chloroethyl)hydrazines as antineoplastic agents", J Med Chem 36:3496-502.

Shyam, et al., 1996, Antitumor 2-(aminocarbonyl)-1,2-bis(methylsulfonyl)-1-(2-chloroethyl)- hydrazines, J Med Chem 39:796-801.

Giles, et al., 2004, "A Phase I and Pharmacokinetic Study of VNP40101M, a Novel Sulfonylhydrazine Alkylating Agent, in Patients with Refractory Leukemia.", Clinical Cancer Research, vol. 10, pp. 2908-2917.

Ishiguro, et al., 2005, "Role of 0-alkylguanine-DNA alkyltransferase in the cytotoxic activity of clorezatine", Mol Cancer Ther, vol. 4 (11), pp. 1755-1763.

Rice, et al., 2005, "Differential inhibition of cellular glutathione reductase activity by isocyanates generated from the antitumor prodrugs Cloretazine and BCNU.", Biochemical Pharmacology, vol. 69, pp. 1463-1472.

PCT International Search Report for VION Pharmaceuticals, et al., Int'l Application No. PCT/US2005/010152, filed Mar. 25, 2005, Dated Mar. 21, 2006.

Lee, et al., "Toxicological evaluation of 1,2 bis(methylsulfonyl)-1-(2-chloroethyl)-2 (methylaminocarbonyl) hydrazine (VNP40101M), novel alkylating Agent with Potential Antitumor Activity, with Intravenous Administration in Rats and Dogs"., International Journal of Toxicology, vol. 23, pp. 23-29 (2002).

Ishiguro, et al., "Role of 0-alkylguanine-DNA alkyltransferase in the cytotoxic activity of clorezatine", Mol Cancer Ther, vol. 4 (11), pp. 1755-1763 (2005).

Murren, et al., "A phase I and pharmacokinetic study of VNP4010M, a new alkylating agent, in patients with advanced or metastatic cancer"., Investigational New Drugs, vol. 23, pp. 123-135 (2005).

Giles, et al., "A Phase I and Pharmacokinetic Study of VNP40101M, a Novel Sulfonylhydrazine Alkylating Agent, in Patients with Refractory Leukemia.", Clinical Cancer Research, vol. 10, pp. 2908-2917 (2004).

Rice, et al., "Differential inhibition of cellular glutathione reductase activity by isocyanates generated from the antitumor prodrugs Cloretazine and BCNU.", Biochemical Pharmacology, vol. 69, pp. 1463-1472 (2005).

PCT International Preliminary Report on Patentability for VION Pharmaceuticals, et al., Int'l Application No. PCT/US2005/010152. Filed Mar. 25, 2005, Dated Sep. 26, 2006.

International Search Report issued Mar. 21, 2006 for Vion Pharmaceuticals, Inc, et al., International Publication No. WO/2005/094282.

Written Opinion of the International Searching Authority, issued Mar. 21, 2006 for Vion Pharmaceuticals, Inc, et al., International Publication No. WO/2005/094282.

Penketh, et al., 1986, "Mechanisms of resistance to alkylating agent", Cancer Treat Res 87:65-81.

U.S. Appl. No. 60/556,565, filed Mar. 26, 2004, King et al.

Finch et al., Apr. 1, 2001, "1,2-Bis(methylsulfonyl)-1-(2-chloroethyl)-2-(methylamino)carbonylhydrazine (101M): A Novel Sulfonylhydrazine Prodrug with Broad-Spectrum, Antineoplastic Activity", Cancer Research, vol. 61(7):3033-3038.

\* cited by examiner

COMBINATION THERAPY COMPRISING CLORETAZINE

This application claims benefit of U.S. Ser. No. 60/556,565, filed Mar. 26, 2004. The content of this preceding application is hereby incorporated in its entirety by reference into this application.

Throughout this application, various publications are referenced. Disclosures of these publications in their entireties are hereby incorporated by reference into this application in order to more fully describe the state of the art to which this invention pertains.

FIELD OF THE INVENTION

This invention relates to combination therapy comprising Cloretazine™. This invention further relates to synergistic effects of Cloretazine™ and nucleosides.

BACKGROUND OF THE INVENTION

Alkylating agents are among the most effective therapeutic agents currently available to treat different malignancies, and are widely used in the clinic (Katzung, In *Basic & Clinical Pharmacology*, 7th edition, 1998, Appleton & Lange, Stamford, 881). The high degree of cytotoxicity is attributed to the ability to induce DNA interstrand cross-linking thereby inhibiting replication (Rajski and Williams, *Chem Reviews* 1998, 98: 2723). Among the alkylating agents, the CNU (chloroethylnitrosourea) series have been widely used clinically to treat brain tumors, colon cancer and lymphomas (DeVita, et al. *Cancer Res.* 1965, 25: 1876; and Nissen, et al. *Cancer* 1979, 43: 31), however, their clinical usefulness is limited due to delayed and cumulative bone marrow depression and hepatic toxicity (Panasci, et al. *Cancer Res.* 1977, 37: 2615; and Gibson and Hickman, *Biochem Pharmacol.* 1982, 31: 2795).

A series of 1,2-bis(sulfonyl)hydrazine prodrugs (SHPs) with the ability to generate chloroethylating and carbamoylating species, but lacking hydroxyethylating and vinylating species, generated by the CNUs had been developed recently (Sartorelli, et al. see U.S. Pat. No. 6,040,338; U.S. Pat. No. 5,637,619; U.S. Pat. No. 5,256,820; U.S. Pat. No. 5,214,068; U.S. Pat. No. 5,101,072; U.S. Pat. No. 4,849,563; and U.S. Pat. No. 4,684,747). The antitumor activity has been suggested to result from chloroethylating and subsequent cross-linking of DNA (Kohn, In *Recent Results in Cancer Research*, Eds. Carter, et al., 1981, Springer, Berlin, vol. 76: 141; and Shealy, et al., *J Med Chem.* 1984, 27: 664). The carbamoylating species (i.e., the isocyanate) can react with thiol and amine functionalities on proteins and inhibit DNA polymerase (Baril, et al. *Cancer Res.* 1975, 35: 1), the repair of DNA strand breaks (Kann, et al. *Cancer Res.* 1974, 34: 398) and RNA synthesis and processing (Kann, et al. *Cancer Res.* 1974, 34: 1982). However, hydroxyethylation of DNA is a carcinogenic and/or mutagenic event (Swenson, et al. *J Natl Cancer Inst.* 1979, 63: 1469).

1,2-Bis(methylsulfonyl)-1-(2-chloroethyl)-2-(methylaminocarbonyl) hydrazine (VNP40101M, Cloretazine™), the current lead compound in the SHP series, has lower toxicity to hosts and better anti-tumor activities against the L1210 murine leukemia, L1210/BCNU, L1210/CTX, L1210/MEL (1,3-bis(2-chloroethyl)-1-nitrosourea, cyclophosphamide and melphalan resistant sublines), P388 leukemia, M109 lung carcinoma, B16 melanoma, C26 colon carcinoma and U251 glioma than chloroethylnitrosourea (CNU) derivatives and other SHP analogs (Shyam, et al. *J Med Chem.* 1999, 42: 941). In addition, VNP40101M is effective in crossing the blood brain barrier (BBB) and eradicating leukemia cells implanted intracranially (>6.54 log cell kill), rivaling the efficacy of BCNU (Finch, et al. *Cancer Biochem Biophys.* 2001, 61: 3033).

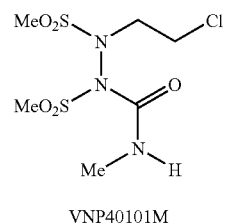

VNP40101M

The anti-tumor activity of VNP40101M is probably due to the release of 90CE and methyl isocyanate. 90CE further fragments to yield methyl 2-chloroethyldiazosulfone (1), see FIG. 1 of U.S. Pat. No. 6,855,695, a relatively specific $O^6$-guanine chloroethylator, producing minimal alkylation of the $N^7$-position of guanine (Penketh, et al. *J Med Chem.* 1994, 37: 2912; and Penketh, et al. *Biochem Pharmacol.* 2000, 59: 283). Methyl isocyanate released from VNP40101M has the ability to inhibit various DNA repair enzymes including $O^6$-alkylguanine-DNA alkyltransferase leading to stabilization of the $O^6$-alkylguanine monoalkyl species in DNA, which leads to a larger percentage of interstrand cross-links (Baril, et al. *Cancer Res.* 1975, 35: 1)

Activity in Murine Tumor Models

VNP40101M has shown broad anti-tumor activity against leukemia and solid syngeneic and human xenograft tumors in murine models (Shyam et el., J Med Chem 28:525-7, 1985; Shyam et al., J Med Chem 29:1323-5, 1986; Shyam et al., J Med Chem 30:2157-61, 1987; Shyam et al., J Med Chem 36:3496-502, 1993; Shyam et al., J Med Chem 39:796-801, 1996). The data is summarized briefly below:

1. Against intraperitoneal (IP) implanted L1210 leukemia ($10^6$ tumor cells) that is resistant to 1,3-bis(2-chloroethyl)-1-nitrosourea (BCNU), cyclophosphamide, or melphalan, a single dose of VNP40101M administered IP 24 hours after tumor inoculation (20-60 mg/kg, or 60-180 mg/m$^2$) was curative in 100% of mice (survival $\geq$60 days). The VNP40101M doses required to produce long-term survival in sensitive and resistant L1210-bearing mice were only modestly myelosuppressive when administered to non-tumor-bearing mice. Higher single doses (80-100 mg/kg) produced signs of a wasting condition and death in some animals, which occurred >50 days after treatment. When administered IP daily for 6 days, VNP40101M at a dose of 6 mg/kg/d (total dose 36 mg/kg) increased life span of treated mice by 333% compared to control mice, and at doses of 12-18 mg/kg/d (total doses of 72-108 mg/kg) was curative in 100% of animals. Delayed toxic deaths were not observed with the d×6 schedule, however, total doses higher than 108 mg/kg were not tested.

2. Against subcutaneous tumors of the human U251 glioma staged to ~300 mg in nude mice, VNP40101M administered as 10 mg/kg q2d×11 or 20 mg/kg q4d×6 IP caused complete regressions.

3. Against the murine M109 lung carcinoma implanted subcutaneously and staged to ~150 mg, VNP40101M administered as 10 mg/kg q2d×10 or 20 mg/kg q4d×5 IP delayed tumor growth, with the latter schedule delaying time to reach 1 gram by 14 days.

4. Administration of VNP40101M weekly by the IP route produced significant delays in tumor growth against the syngeneic B16F10 melanoma and against the human HTB177 lung (H460) and WiDr colon carcinoma cell lines. Doses from 10-60 mg/kg were active, but higher doses produced greater growth inhibition.

5. Substantial anti-tumor activity was observed by IP administration of VNP40101M against intra-cranially implanted L1210 leukemia, demonstrating good penetration through the blood-brain barrier.

Toxicology Studies

The relationship between VNP40101M dose and white blood cell count (WBC) was examined in normal $CD_2F_1$ mice. Modest leukopenia (50% of baseline) was observed with a single IP dose of 40 mg/kg (120 mg/m$^2$). VNP40101M doses of 60-80 mg/kg reduced WBC counts to approximately 25 and 15% of baseline, respectively, by day 4 with full recovery by day 21. As noted in section 1.2.A, high single doses of 80-100 mg/kg administered IP to tumor-bearing mice produced signs of a wasting condition and deaths occurring >50 days after treatment.

Toxicology studies were performed in rats. A dose of 3 mg/kg (18 mg/m$^2$), when given intravenously (IV) on a d×5 dosing schedule, produced no clinical signs or symptoms on day 15, but 2/10 rats had lung findings on day 29, including a small amount of thoracic cavity fluid and failure of the lung to collapse. Microscopic findings at the 3 mg/kg (d×5) dose level were primarily limited to the lung and included alveolar edema, congestion, alveolar histiocytosis, and vascular thrombi. The higher dose of 10 mg/kg (60 mg/m$^2$) d×5 produced few significant gross necropsy findings on day 15, but thoracic cavity fluid was found in approximately 50% of animals sacrificed on day 29 and 6/6 animals sacrificed on days 30/31. Histopathologic findings in the lung were similar to those observed at the 3 mg/kg dose level. For doses as high as 10 mg/kg d×5, myelosuppression was not observed. Effects on serum chemistries were limited to decreases in total protein and albumin, which were observed on day 29 in the 10 mg/kg dose group.

In toxicology studies performed in dogs, single doses of 1, 3, 10, and 30 mg/kg were administered intravenously. The 1 and 3 mg/kg doses were well-tolerated and produced minimal clinical signs through at least 21 days of observation. The higher doses of 10 and 30 mg/kg (200 and 600 mg/m$^2$, respectively) produced marked clinical signs, as well as laboratory abnormalities including increased alkaline phosphatase, decreased albumin, increased bilirubin, increased creatine phosphokinase, and decreased white and red blood cell counts. Toxicity was also assessed for 0.3, 1 and 3 mg/kg doses administered intravenously daily×5. The 3 mg/kg d×5 dose produced marked clinical signs including reduced activity, loose stool, anorexia and slight dehydration, requiring sacrifice of the animals on day 8. There was also marked leukopenia by day 8, and slight elevation of the alkaline phosphatase. A dose of 1 mg/kg (20 mg/m$^2$) d×5 produced minimal clinical signs and symptoms, and only a mild leukopenia on day 8 that recovered to baseline by day 15.

Phase I Studies of VNP40101M

VNP40101M has been studied in two phase I trials conducted in patients with advanced solid tumors or hematologic malignancies. In the first phase I trial, 26 patients with solid tumors were treated by IV infusion over 15-30 minutes at dose levels ranging from 3-305 mg/m$^2$ every 4-6 weeks. The maximum tolerated dose (MTD) was 305 mg/m$^2$. Among the seven patients treated at the MTD, six developed grade 3 thrombocytopenia. The platelet nadir occurred between days 25-33. Five of the patients treated at the MTD developed ≧grade 2 granulocytopenia, but only one patient had a grade 3 event. Hematologic toxicities recovered to ≦ grade 1 between days 32-45. No dose-limiting non-hematologic toxicities were observed.

A second phase I trial is being conducted at the MD Anderson Cancer Center in patients with advanced hematologic malignancies. Twenty-eight patients with relapsed or refractory leukemia (20 acute myeloid leukemia [AML], 3 myelodysplasia, 1 chronic myeloid leukemia in blast crisis, 3 acute lymphocytic leukemia, 1 chronic lymphocytic leukemia) have been accrued to the study at doses ranging from 220-708 mg/m$^2$. Through the dose of 708 mg/m$^2$, no dose-limiting non-hematologic toxicities were observed. At doses ≧400 mg/m2, patients developed a transient infusion-related syndrome consisting of headache, nausea, vomiting, myalgias/cramps, facial flushing, dizziness, tachycardia, and hypotension. The infusion-related reaction was self-limited and resolved within several hours after completing treatment in all patients. Among the seven patients treated at 708 mg/m$^2$, one patient developed prolonged marrow aplasia (>80 days) without evidence of leukemia. Thus, myelosuppression may be a dose-limiting toxicity (DLT) at 708 mg/m$^2$. An additional cohort of patients is currently being evaluated at an interim dose of 600 mg/m$^2$.

Evidence of anti-tumor activity was observed in patients with advanced hematologic malignancies. One previously untreated patient with high-risk myelodysplasia developed a complete response by day 28 after a single course of VNP40101M administered at 300 mg/m$^2$. Although no other patient achieved complete remission, VNP40101M reduced peripheral blood blasts at least transiently in most patients at all dose levels. In addition, a heavily pre-treated patient with AML had substantial clearing of marrow blasts and resolution of gingival leukemic infiltration at a dose of 220 mg/m$^2$, and a patient with AML treated at 532 mg/M$^2$ had reduction in marrow blasts and improvement of neutrophil counts by day 28. The level of activity warrants further exploration of VNP40101M alone and in combination in patients with AML.

SUMMARY OF THE INVENTION

This invention provides a method for treating tumor in a subject comprising administering to the subject an effective amount of: (1) VNP40101M, or its equivalent; and (2) a nucleoside, or a nucleoside analog. This invention also provides a method for inhibiting tumor cell growth comprising contacting the tumor cell with effective amounts of: (1) VNP40101M, or its equivalent; and (2) a nucleoside, or a nucleoside analog.

The present invention relates to the treatment of cancer, comprising administering to a subject in need thereof an effective amount of VNP40101M in combination with a nucleoside.

This invention provides a composition comprising an amount of VNP40101M which produces synergistic effects when used in combination with a nucleoside in treating tumor.

This invention provides a composition comprising an amount of nucleoside which produces synergistic effects when used in combination with a VNP40101M in treating tumor.

This invention provides a composition comprising an amount of an anticancer agent which produces synergistic effects when used in combination with a VNP40101M in treating tumor.

This invention provides other cancer therapies such as radiation or other chemotherapeutics which include, but are not limited to, antimetabolites, etoposide, doxorubicin, taxol, vincristine, cyclophosphamide, mitomycin C, topoisomerase I and topoisomerase II inhibitors (adriamycin, topotecan, campothecin and irinotecan), platinum containing compounds, (cisplatin, carboplatin), tipifarnib (R115777), SCH66336, erlotinib, gefitinib, and gemtuzumab ozogamicin, may be used with VNP40101M or its equivalent. VNP40101M or its equivalent provides synergistic effects when used in combination with these therapies.

DETAILED DESCRIPTION OF THE INVENTION

This invention provides a method for treating tumor in a subject comprising administering to the subject an effective amount of: (1) VNP40101M, or its equivalent; and (2) a nucleoside, or a nucleoside analog. This invention also provides a method for inhibiting tumor cell growth comprising contacting the tumor cell with effective amounts of: (1) VNP40101M, or its equivalent; and (2) a nucleoside, or a nucleoside analog.

VNP40101M -Cloretazine™

VNP40101M is a representative form of SHPs. As used herein, VNP40101M covers itself, its salt or other prodrug forms which produce same or similar effective in vivo. Prodrug is an inactive precursor which will be converted into its active form by normal metabolic processes.

VNP40101M and its equivalents are known in the art. See e.g. U.S. Pat. No. 6,855,695 B2, issued Feb. 15, 2005. Other SHPs can also be used in the invention.

The present invention relates to the treatment of cancer, comprising administering to a subject in need thereof an effective amount of VNP40101M in combination with a nucleoside.

These agents may be administered concurrently or sequentially.

In an embodiment, the subjects are mammals. In a further embodiment, the subjects are human.

Nucleosides and their Analogs

As used herein, the nucleoside analog is defined as analog which produces substantially the same effect as the nucleoside itself. Nucleoside analogs are capable of inhibiting DNA synthesis or incorporating into DNA such as azacitidine, cladribine, decitabine. gemcitabine, mercaptopurine, thioguanine, fludarabine, clofarabine, troxacitabine, and pentostatin are useful to combine with VNP40101M to treat malignancies.

Cytarabine, a cell-cycle specific antimetabolite, is the most effective drug in the treatment of AML. Cytarabine is phosphorylated intracellularly and incorporated into DNA. By inhibiting DNA polymerases and DNA synthesis, cytarabine is predicted to inhibit DNA repair and enhance the cytotoxicity of VNP40101M.

Radiation or other Chemotherapeutics

Other cancer therapies such as radiation or other chemotherapeutics which include, but are not limited to, antimetabolites, etoposide, doxorubicin, taxol, vincristine, cyclophosphamide, mitomycin C, topoisomerase I and topoisomerase II inhibitors (adriamycin, topotecan, campothecin and irinotecan), platinum containing compounds, (cisplatin, carboplatin), tipifarnib (R115777), SCH66336, erlotinib, gefitinib, and gemtuzumab ozogamicin, may be used with VNP40101M or its equivalent. VNP40101M or its equivalent provides synergistic effects when used in combination with these therapies.

An aspect of the present invention relates to the treatment of cancer, comprising administering to a patient in need thereof an effective amount of VNP40101M in combination with at least one therapeutic agent. In an embodiment, the agent is a nucleoside or a nucleoside analog.

The treatment of solid malignant tumors, leukemia, and lymphomas is a preferred embodiment of the present invention. In a further embodiment, the cancer is acute myelogenous leukemia (AML).

The amount of VNP40101M and nucleoside or its analog used according to the present invention is an effective amount for treating cancer. In general, a therapeutically effective amount of the VNP40101M according to the present invention usually ranges from less than about 0.05 mg/kg to about 100 mg/kg of body weight of the patient to be treated, or considerably more, depending upon the compound used, the tumor type to be treated, the ability of the active compound to localize in the tissue to be treated, the route of administration and the pharmacokinetics of the compound in the patient.

VNP40101M is preferably administered in amounts ranging from about 0.5 mg/kg (17.5 mg/m$^2$) to about 50 mg/kg (1750 mg/M$^2$) or more at one time. Nucleoside or its analog is preferably administered in amounts ranging from about 0.1 mg/kg (3.5 mg/m$^2$) to about 150 mg/kg (5250 mg/m$^2$) or more at one time; preferably is given from 1 mg/kg to 100 mg/kg. The duration of treatment may be for one or more days or may last for several months or considerably longer (years) depending upon the disease state treated.

In a more preferred embodiment, VNP40101M is given to the patient at doses of 1 mg/kg to 20 mg/kg and the nucleoside at doses of 10 mg/kg to 80 mg/kg. In another preferred embodiment, the nucleoside is cytarabine (AraC) and the dose ranges from 20 mg/kg to 60 mg/kg. In a still further embodiment the does of VNP40101M is between 100 and 1000 mg/m$^2$ and the dose of AraC is between 500 and 5000 mg/m$^2$.

Synergistic Effects

This invention provides a composition comprising an amount of VNP40101M or its equivalent which produces synergistic effects when used in combination with a nucleoside or its analog in treating tumor.

This invention provides a composition comprising an amount of nucleoside which produces synergistic effects when used in combination with a VNP40101M in treating tumor.

As demonstrated in the below examples, this effective amount of either VNP40101M, its equivalent or nucleoside (its analog), can be routinely determined. These combinations of agents may be delivered intravenously, subcutaneously, intramuscularly, intraperitoneally or orally. Other routes of administration such as inhalation may also be used.

This invention will be better understood from the examples which follow. However, one skilled in the art will readily appreciate that the specific methods and results discussed are merely illustrative of the invention as described more fully in the claims which follow thereafter.

Experimental Details

Example 1

In vitro Cytotoxicity of VNP40101M and AraC (Cytarabine) on Tumor Cell Lines

The cytotoxicity of the combination of VNP40101M and Arac on L1210 leukemia was examined using a cell viability assay. Cells were exposed to VNP40101M, alone or in combination with various concentrations of AraC. After 72 hours, the remaining viable cells were quantified by measuring mitochondrial oxidoreductase activity. Concentrations of AraC and VNP40101M used were between 0.75 and 6 uM. Dose-effect analyses (combination index) showing combination effects of VNP40101M and AraC were analyzed. Combination indices of 0.75-0.8 and 0.1-0.3 indicate moderate synergism and strong synergism, respectively (Chou and Talalay, *Adv. Enz. Regul.*, 22, 27-55, 1984). Cytotoxic effect of VNP40101M was evaluated in the presence of AraC on L1210 leukemia and table 1 shows that CLOETAZINE worked synergistically with AraC on leukemia.

TABLE 1

Combination of AraC and VNP40101M after 1 hour exposure to L1210 Cells.

| AraC (μM) | VNP40101M (μM) | Fraction affected | Combination Index* |
|---|---|---|---|
| 0.75 | 6 | 0.955 | 0.243 |
| 0.75 | 3 | 0.915 | 0.189 |
| 0.75 | 1.5 | 0.904 | 0.121 |
| 0.75 | 0.75 | 0.886 | 0.089 |
| 1.5 | 6 | 0.962 | 0.246 |
| 1.5 | 3 | 0.918 | 0.221 |
| 1.5 | 1.5 | 0.918 | 0.147 |
| 1.5 | 0.75 | 0.903 | 0.122 |
| 3 | 6 | 0.967 | 0.271 |
| 3 | 3 | 0.928 | 0.273 |
| 3 | 1.5 | 0.925 | 0.209 |
| 3 | 0.75 | 0.924 | 0.175 |
| 6 | 6 | 0.958 | 0.405 |
| 6 | 3 | 0.943 | 0.357 |
| 6 | 1.5 | 0.933 | 0.325 |
| 6 | 0.75 | 0.925 | 0.312 |

Example 2

In Vitro Cytotoxicity of VNP40101M and Fludarabine on Tumor Cell Lines

The cytotoxicity of the combination of VNP40101M and nucleoside analogs on tumor cell lines is examined using a cell viability assay. Several leukemia cell lines (L1210 and HL-60) and lymphoma cell lines (Raji and Namalwa) are exposed to VNP40101M, alone or in combination with various concentrations of Fludarabine. After 72 hours, the remaining viable cells were quantified by measuring mitochondrial oxidoreductase activity. Concentrations of Fludarabine used are between 0.1 to 100 uM; concentrations of VNP40101M used are between 0.1 to 100 uM. Dose-effect analyses (combination index) showing combination effects of VNP40101M and Fludarabine are analyzed. Combination indices of 0.75-0.8 and 0.1-0.3 indicate moderate synergism and strong synergism, respectively.

Example 3

In Vivo Antitumor Activity of VNP40101M and AraC on Leukemia

Eighty Female Balb/c×DBA/2 (CD$_2$F1) mice were inoculated intraperitoneally (ip) on day 0 with $1 \times 10^6$ L1210 cells in 0.2 mL phosphate-buffered-saline (PBS). The mice were randomly divided into 6 groups; each group consisted of 10 mice. The animals were untreated or treated with a single bolus dose of VNP40101M at 5, or 10 mg/kg, ip, on day 1 with or without AraC (50 mg/kg, ip) on days 1, 3, 5, 7, and 9. Daring the experiments, mice were observed daily for survival. It was determined that mice that survive for more than 60 days after inoculation of L1210 cells might be regarded as long-term survivors. Kaplan-Meier plots were generated, and survival time of animals was analyzed using student T-test. Significance was defined as $P<0.05$.

Table 2 shows that intraperitoneal inoculation of mice with $1 \times 10^6$ L1210 leukemia cells resulted in a rapid development of ascites followed by death of all animals in untreated control within 18 days and in AraC treatment control within 30 day. VNP40101M treatment at single doses of 5 and 10 mg/kg increased long-term survivors to 50% and 90%, respectively. Therapeutic efficacies or combinational treatments were superior to single agents. VNP40101M, at 5 and 10 mg/kg, plus AraC treatments increased long-term survivors to 80% and 100%, respectively. Our results suggest that VNP40101M significantly enhanced anti-tumor effect of AraC.

TABLE 2

Therapeutic efficacy of single agents vs. combinations

| Group | Long-term Survivors (%) | P value* |
|---|---|---|
| 1. Untreated Control | 0 | |
| 2. AraC 50 mpk | 0 | |
| 3. VNP40101M 5 mpk | 50 | |
| 4. VNP40101M 10 mpk | 90 | |
| 5. AraC 50 mpk + VNP40101M 5 mpk | 80 | 0.0024 |
| 6. AraC 50 mpk + VNP40101M 10 mpk | 100 | 0.0022 |

*Combinational therapy against VNP40101M at corresponding doses

Example 4

In Vivo Antitumor Activity of VNP40101M and Fludarabine on Leukemia

Eighty Female Balb/c×DBA/2 (CD$_2$F1) mice are inoculated intraperitoneally (ip) on day 0 with $3 \times 10^6$ L1210 cells in 0.2 mL phosphate-buffered-saline (PBS). The mice are randomly divided into 6 groups; each group consists of 10 mice. The animals are untreated or treated with a single bolus dose of VNP40101M at 5, or 10 mg/kg, ip, on day 1 with or without fludarabine (70 mg/kg, ip) on multiple days between days 1 to 9. During the experiments, mice are observed daily for survival. It is determined that mice that survive for more than 60 days after inoculation of L1210 cells might be regarded as long-term survivors. Kaplan-Meier plots are generated, and survival time of animals is analyzed using student T-test. Significance is defined as $P<0.05$.

Table 3 shows that intraperitoneal inoculation of mice with $3 \times 10^6$ L1210 leukemia cells resulted in a rapid development of ascites followed by death of all animals in untreated control within 18 days and in fludarabine treatment control within 30 day. VNP40101M treatment at single doses 10 mg/kg increased long-term survivors to 40%. Therapeutic efficacy of combinational treatment was superior to single agents. VNP40101M, at 10 mg/kg plus fludarabine treatments increased long-term survivors to 90%. Our results suggest that VNP40101M significantly enhanced anti-tumor effect of fludarabine.

TABLE 3

Therapeutic efficacy of single agents vs. combinations

| Group | Long-term Survivors (%) | P value* |
|---|---|---|
| 1. Untreated Control | 0 | |
| 2. Fluda 70 mpk | 0 | |
| 3. VNP40101M 5 mpk | 0 | |
| 4. VNP40101M 10 mpk | 40 | |
| 5. Fluda 70 mpk + VNP40101M 5 mpk | 0 | |
| 6. Fluda 70 mpk + VNP40101M 10 mpk | 90 | 0.0025 |

Example 5

Use of VNP40101M and AraC in Patients with AML

AraC is administered by IV contiguous infusion at a dose of 0.5 to 4.0 gm/m²/day for one to six days. Preferably, AraC is administered at a dose of 1.0 to 2.0 gm/m²/day for three to four days. VNP40101M is administered over 15-30 minutes on day 1 to day 3 after AraC infusion. The dose of VNP40101M is between 200 to 700 mg/m². Preferably, VNP40101M is administered one day after AraC infusion and the dose is between 450 to 650 mg/m². Multiple cycles of treatment can be repeated.

Example 6

Use of VNP40101M and Clofarabine in Patients with AML

Clofarabine is administered by IV at a dose of 10 to 50 mg/m²/day for one to six days. Preferably, clofarabine is administered at a dose of 30 to 40 mg/m²/day for five consecutive days. VNP40101M is administered over 15-60 minutes as a single bolus injection before, during, or after clofarabine administration. The dose of VNP40101M is between 200 and 700 mg/m². Preferably, VNP40101M dose is between 450 and 650 mg/m². Multiple cycles of treatment can be repeated.

Example 7

Use of VNP40101M and Tipifarnib in Patients with AML

Tipifarnib is administered orally at 200 to 800 mg/dose, one to three doses a day for up to 28 days. Preferably, tipifarnib is administered at 600 mg/dose, two doses per day, for 28 consecutive days. VNP40101M is administered over 15-60 minutes as a single bolus injection before, during, or after administration of tipifarnib. The dose of VNP40101M is between 200 to 700 mg/m². Preferably, VNP40101M is between 450 and 650 mg/m². Multiple cycles of treatment can be repeated.

REFERENCES

1. Shyam K, Cosby L A, Sartorelli A C: Synthesis and evaluation of N,N'-bis(arylsulfonyl)hydrazines as antineoplastic agents. J Med Chem 28:525-7, 1985
2. Shyam K, Furubayashi R, Hrubiec R T, et al: 1,2-bis (arylsulfonyl)hydrazines. 2. The influence of arylsulfonyl and aralkylsulfonyl substituents on antitumor and alkylating activity. J Med Chem 29:1323-5, 1986
3. Shyam K, Hrubiec R T, Furubayashi R, et al: 1,2-Bis (sulfonyl)hydrazines. 3. Effects of structural modification on antineoplastic activity. J Med Chem 30:2157-61, 1987
4. Shyam K, Penketh P G, Divo A A, et al: Synthesis and evaluation of 1-acyl-1,2-bis(methyl sulfonyl)-2-(2-chloroethyl)hydrazines as antineoplastic agents. J Med Chem 36:3496-502, 1993
5. Shyam K, Penketh P G, Loomis R H, et al: Antitumor 2-(aminocarbonyl)-1,2-bis(methylsulfonyl)-1-(2-chloroethyl)-hydrazines. J Med Chem 39:796-801, 1996.
6. Penketh P G, Shyam K, Sartorelli A C: Comparison of DNA lesions produced by tumor-irihibitory 1,2-bis(sulfonyl)hydrazines and chloroethylnitrosoureas. Biochem Pharmacol 59:283-91, 2000
7. Pratviel G, Shyam K, Sartorelli A C: Cytotoxic and DNA-damaging effects of 1,2-bis(sulfonyl)hydrazines on human cells of the Mer+ and Mer– pnenotype. Cancer Biochem Biophys 10:365-75, 1989
8. Penketh P G, Shyam K, Sartorelli A C: Mechanisms of resistance to alkylating agents. Cancer Treat Res 87:65-81, 1996
9. Penketh P G, Shyam K, Sartorelli A C: Studies on the mechanism of decomposition and structural factors affecting the aqueous stability of 1,2-bis(sulfonyl)-1-alkylhydrazines. J Med Chem 37:2912-7, 1994
10. Giles F, Thomas D, Garcia-Manero G, et al: A Phase I and pharmacokinetic study of VNP40101M, a novel sulfonylhydrazine alkylating agent, in patients with refractory leukemia. Clinical Cancer Research 10(9): 2908-2917, 2004
11. Murren J, Modiano M, Kummar S, et al: A phase I and pharmacokinetic study of VNP40101M, a new alkylating agent, in patients with advanced or metastatic cancer. Invest New Drugs 23(2):123-135, 2005
12. Baumann R P, Shyam K, Penketh P G, et al: 1,2-Bis (methylsulfonyl)-1-(2-chloroethyl)-2-[(methylamino) carbonyl] hydrazine (VNP40101M): II. Role of O6-alkylguanine-DNA alkyltransferase in cytotoxicity. Cancer Chemother Pharmacol. 53(4):288-295, 2004
13. Mao J, Xu Y, Wu D, et al: Pharmacokinetics, Mass Balance, and Tissue Distribution of a Novel DNA Alkylating Agent, VNP40101M, in Rats. AAPS PharmSci 4 (4)24, 2002
14. Lee K C, Almassian B, and Noveroske J: Toxicological evaluation of 1,2-bis(methylsulfonyl)-1-(2-chloroethyl)-2-(methylaminocarbonyl) hydrazine (VNP40101M), novel alkylating agent with potential antitumor actively, with intravenous administration in rats and dogs. Int J Toxicol. 21(1):23-38, 2002

What is claimed is

1. A composition comprising a dosage of 5 mg/kg to 10 mg/kg of 1,2-Bis-(methylsulfonyl)-1-(2-chloroethyl)-2-(methylaminocarbonyl)-hydrazine (VNP40101M) and a dosage of about 50 mg/kg of cytarabine, wherein the VNP40101M and cytarabine produce synergistic effects when used in combination in treating tumor.

2. A composition comprising a dosage of 5 mg/kg to 10 mg/kg of VNP40101M and a dosage of about 70 mg/kg of fludarabine, wherein the VNP40101M and fludarabine produce synergistic effects when used in combination in treating tumor.

3. A method of treating tumor in a subject, comprising the step of administering to the subject 5 mg/kg to 10 mg/kg of VNP40101M and about 50 mg/kg cytarabine, wherein the amounts of VNP40101M and cytarabine administered provide, a reduction in tumor growth that is larger than that achieved by administering either VNP40101M or cytarabine individually.

4. The method of claim 3, wherein the tumor is solid malignant tumor, leukemia or lymphoma.

5. The method of claim 3, wherein VNP40101M and cytarabine are administered concurrently or sequentially.

6. The method of claim 3, wherein VNP40101M and cytarabine are administered intravenously, subcutaneously, or orally.

7. The method of claim 4, wherein the leukemia is acute myelogenous leukemia.

8. A method of treating tumor in a subject, comprising administering to the subject between 100 and 1000 mg/m$^2$ of VNP40101M and between 500 and 5000 mg/m$^2$ cytarabine, wherein the amounts of VNP40101M and cytarabine administered provide a reduction in tumor growth that is larger than that achieved by administering either VNP40101M or cytarabine individually.

9. The method of claim 3, wherein the subject is a human.

10. A method of treating tumor in a subject, comprising the step of administering to the subject 5 mg/kg to 10 mg/kg VNP40101M and about 70 mg/kg fludarabine, wherein the amounts of VNP40101M and fludarabine administered provide a reduction in tumor growth that is larger than that achieved by administering either VNP40101M or fludarabine individually.

11. The method of claim 10, wherein the tumor is solid malignant tumor, leukemia or lymphoma.

12. The method of claim 10, wherein VNP40101M and fludarabine are administered concurrently or sequentially.

13. The method of claim 10, wherein VNP40101M and fludarabine are administered intravenously, subcutaneously, or orally.

14. The method of claim 11, wherein the leukemia is acute myelogenous leukemia.

15. The method of claim 10, wherein the subject is a human.

* * * * *